United States Patent [19]

Nozoe et al.

[11] Patent Number: 5,556,533
[45] Date of Patent: Sep. 17, 1996

[54] VOLTAGE APPLYING METHOD FOR HYDROGEN-TYPE ENZYME ELECTRODE

[75] Inventors: Yoshiteru Nozoe; Kazuharu Murata, both of Kitamoto, Japan

[73] Assignee: A & D Company Limited, Tokyo, Japan

[21] Appl. No.: 471,779

[22] Filed: Jun. 6, 1995

Related U.S. Application Data

[62] Division of Ser. No. 284,116, Aug. 2, 1994.

[30] Foreign Application Priority Data

Aug. 3, 1993 [JP] Japan .................................. 5-192452
Nov. 30, 1993 [JP] Japan ................................ 5-68460 U

[51] Int. Cl.$^6$ .................................................. G01N 27/26
[52] U.S. Cl. ........................ 205/777.5; 204/403; 204/412; 435/817
[58] Field of Search ........................ 205/777.5; 204/403, 204/412; 435/817, 291, 288, 289

[56] References Cited

U.S. PATENT DOCUMENTS

| | | | |
|---|---|---|---|
| 4,528,270 | 7/1985 | Matsunaga | 205/777.5 |
| 4,935,105 | 6/1990 | Churchouse | 204/153.12 |
| 5,407,545 | 4/1995 | Hirose | 205/777.5 |
| 5,409,583 | 4/1995 | Yoshioka et al. | 205/777.5 |
| 5,411,647 | 5/1995 | Johnson et al. | 205/777.5 |
| 5,496,452 | 3/1996 | Hill et al. | 205/777.5 |

FOREIGN PATENT DOCUMENTS 62-156555  7/1987  Japan .
3-80353    8/1991  Japan .

*Primary Examiner*—Bruce F. Bell
*Attorney, Agent, or Firm*—Bacon & Thomas

[57] ABSTRACT

A voltage applying method for a hydrogen type enzyme electrode in a chemical sensor and using a pair of working electrodes, a reference electrode and a counter electrode includes detecting a contact of a test specimen with the enzyme electrode; keeping a potential applied to the working electrodes at a first potential of substantially zero for a first preset time; applying a second potential that is higher than a hydrogen peroxide detect potential to the working electrodes for a second preset time; dropping the second potential to a third potential below zero potential; and sweeping from the first potential to a fourth potential higher than said hydrogen peroxide detect potential at a fixed rate. Other variations of the method are disclosed.

12 Claims, 15 Drawing Sheets

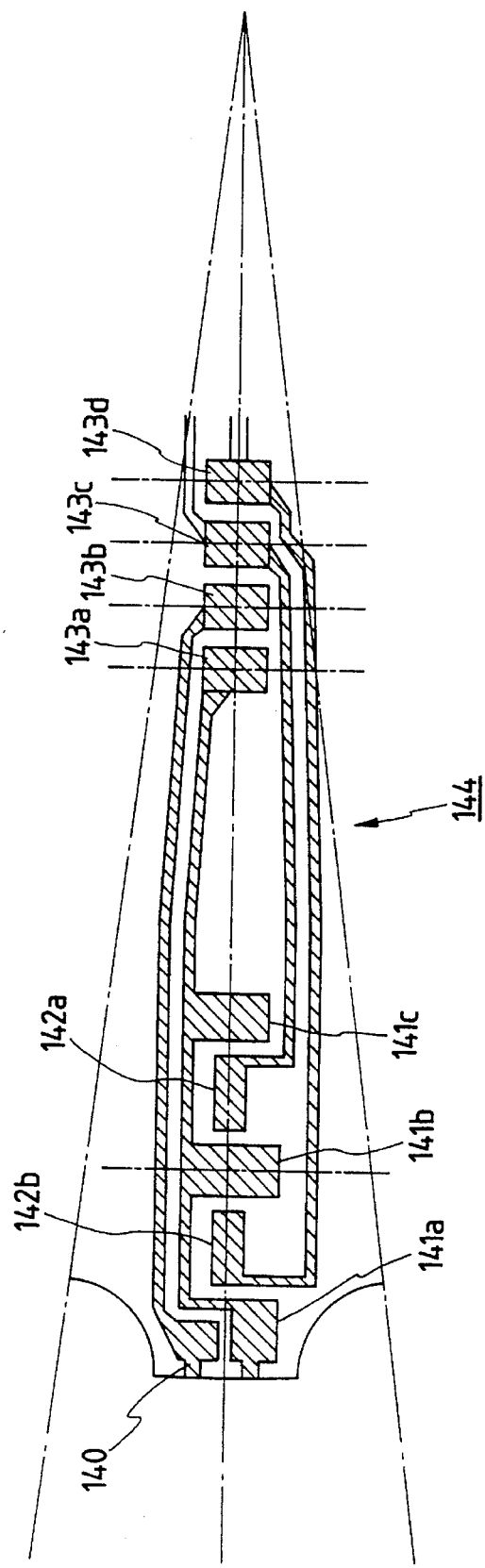

VOLTAGE APPLYING METHOD FOR HYDROGEN-TYPE ENZYME ELECTRODE

CROSS REFERENCE TO RELATED APPLICATIONS

This application is a divisional of U.S. patent application Ser. No. 08/284,116 filed Aug. 2, 1994.

BACKGROUND OF THE INVENTION

1. Field of the Invention

The present invention relates to methods of applying voltage to chemical sensors for example, in a throwaway type chemical sensor.

2. Description of the Related Art

A sensor which converts a given chemical substance contained in a test specimen into an electrical signal for measuring a concentration of the chemical substance has been known. This type of the sensor is called a chemical sensor. For the purposes of easy handling and improving the measuring accuracy, improved chemical sensors have been proposed. Some of the chemical sensor of this type have reached the stage of practical use.

One of the known chemical sensors is a blood-sugar sensor for measuring a value of blood sugar in the blood as a test specimen. This blood-sugar sensor uses an enzyme electrode including a hydrogen peroxide electrode and an enzyme electrode using an oxidation reduction enzyme for converting oxygen into hydrogen peroxide. The blood as a test specimen is dropped on the chemical sensor electrically coupled with a measuring instrument, and a blood sugar value of the blood is measured. After the measurement, the sensor (electrode) is disconnected from the measuring instrument to throw away. This chemical sensor of the throwaway type is free from troublesome work after measurement, such as calibration of the calibration curve, washing of the electrodes, and the like. In other words, the chemical sensor can be handled in a maintenance free manner. Thus, the handling of the chemical sensor is remarkably improved. Further, this throwaway chemical sensor does not have the problem of the measuring accuracy deterioration according to an insufficient washing or the like.

FIG. 14 is a perspective view showing a sensor holder with a throwaway chemical sensor set thereto, which was proposed in Japanese Utility Model Application No. 1-141108 filed by the inventors of the present Patent Application. As shown in the drawing, the throwaway chemical sensor is a sensor collected body 50 containing a plural number (e.g., 10) of sensor elements S serially arrayed thereon. This sensor strip 50 is housed in a sensor holder 51. The foremost sensor element of these chained sensor elements of the sensor collected body 50 is exposed at the tip 51a of the sensor holder 51. The exposed sensor element is electrically connected to a not shown measuring instrument through a connector 52 and a cord 53. A test specimen is dropped on the exposed sensor element to measure the concentration of a given chemical substance thereof. After the measurement, a slider 54 of the sensor holder 51 is forwarded to project the used sensor element from the tip 51a of the holder so that the sensor element is cut out and thrown away. When the used sensor is cut out, a new sensor has already been placed at the tip 51a of the holder and ready for the next measurement. In this way, the process of cutting out and discarding the used or old sensor and another measurement using a new sensor are repeated for successive measurements.

It is confirmed that the throwaway chemical sensor succeeds in improving the efficiency and the accuracy of the measurement. However, the throwaway chemical sensor has still the following problems which have to be solved.

It is desirable that the sensor collected body mounted in the holder has a lot of sensors so as to improve a workability, for example, reducing the number of setting the sensor collected body to the sensor holder. In the case of the sensor collected body illustrated in the drawing, an increase of the number of the sensor elements leads to an elongation of the sensor collected body. The length of the sensor collected body that is acceptable for the sensor holder is limited, so that the number of the sensor elements contained in the sensor collected body is also limited. Generally, the calibration value for the sensor is set up for each manufacturing lot, and input to the measuring instrument. Where the exchange of the sensor collected body with a new one is frequent, it is highly probable that an operator mistakenly uses the sensor collected body of another lot, and that calibration values are mistakenly input to the instrument.

Further, the sensor element is bent and cut out every measurement. During this cut-out work, the test specimen may accidentally be attached to other portions than the sensor element. A danger of contamination and infection by the specimen inevitably exists.

General chemical sensors easily lose their function by moisture. For this reason, a moisture-proof must be taken for the chemical sensors, particularly when these are not used. If the holder 51 is designed so as to have a completely sealed structure, it is very difficult to store the sensor collected body after unpacked for long time while keeping its performances.

In addition, enzyme electrodes of the current-detect type which detects a concentration of a glucose (dextrose) contained in blood or urine have been known. Some of the enzyme electrodes are of the throwaway type. An example of the enzyme electrode of this type is disclosed in Unexamined Japanese Patent Publication No. Hei. 2-245650. The enzyme electrode has such a structure that an electrode portion is formed on an insulating substrate, and an enzyme reaction layer is formed on the electrode. The enzyme reaction layer contains hydrophilic high polymer substance, oxidation reduction enzyme, and electron acceptor.

In the enzyme electrode thus structured, when a test specimen solution is dropped on the enzyme reaction layer, the oxidation reduction enzyme and the acceptor are dissolved into the test specimen solution so that the enzyme reacts with the substrate (glucose) in the specimen solution to deoxidize the receptor. The concentration of the substrate in the specimen solution is calculated using an oxidization current value obtained after the enzyme reaction completes. However, in the enzyme electrode thus structured, the oxidation reduction enzyme tends to bond to oxygen. Accordingly, the oxygen dissolved and existing in the specimen solution (this oxygen will be referred to as a dissolved oxygen) antagonistically act, so that the reaction progresses under the influence of the oxygen, and an error is caused in the measurement.

Another type of the enzyme electrode is disclosed in Unexamined Japanese Patent Publication No. Hei. 2-129541. The enzyme electrode disclosed is of the called hydrogen peroxide type. In this electrode, a substrate (glucose) in a test specimen solution reacts with the dissolved oxygen using enzyme as catalyst to generate hydrogen peroxide. Measured is a current generated when the generated hydrogen peroxide is oxidized at the electrode. The current value thus measured is used for calculating the concentration of the substrate in the test specimen solution.

The enzyme electrode of the hydrogen peroxide type uses the dissolved oxygen in the test specimen solution. Therefore, it is not necessary to use the electron acceptor, which is indispensable to the enzyme electrode of the current-detect type. No antagonism between the dissolved oxygen and the acceptor takes place in the test specimen solution, thereby eliminating the measurement error problem by the antagonism. Such an advantageous enzyme electrode of the hydrogen peroxide type has still a following technical problem to be solved.

In the case of the enzyme electrode of the hydrogen peroxide type, the substrate reacts with the dissolved oxygen in a test specimen solution, using enzyme as catalyst. During the reaction process, hydrogen ions are generated. Also when the hydrogen peroxide is deoxidized, hydrogen ions are generated. By the generated hydrogen, the concentration of hydrogen ions is varied in the test specimen solution. When the concentration of hydrogen ions is varied, the reproducibility of a detected current and a detection sensitivity of the sensor become worse in accordance with the pH dependency of the enzyme reaction and the electrode reaction. An accuracy of detecting the concentration of a substance under measurement is degraded, and the resultant calibration curve has a poor linearity.

SUMMARY OF THE INVENTION

An object of the present invention is to provide a method for applying voltage to an enzyme electrode of the hydrogen peroxide type which is operable independent of the concentration of the dissolved oxygen, and expands a measurable range of the chemical sensor without a complicated electrode structure.

An example of a throwaway chemical sensor using the present invention includes: substantially disk-shaped sensor body; and a plurality of sensor elements radially extended outward from the circumference thereof, which is formed on the sensor body, each of the sensor having a detecting portion including a plurality of electrodes, and a terminal portion including a plurality of terminals corresponding to the electrodes; wherein the electrodes are electrically connected to the corresponding terminals.

In the example of a throwaway chemical sensor using the present invention, the sensor body has a plurality of notch portions forming a plurality of trapezoidal portion on which at least one of the electrodes of each of sensor element is provided.

In addition, in the example of a throwaway chemical sensor using the present invention, the throwaway chemical sensor is housed in a holder having supporting member for rotatably supporting the sensor body; upper and lower covering members for covering at least the sensor; an opening portion which is formed by notch portions of the members for exposing at least one of the sensor elements to an outside of the holder; rotating member for rotating the sensor body; positioning member which is engaged with the notch portion of the sensor body to rotate the sensor body at predetermined distance; terminal member which is contact with the terminal portion of the sensor element which is exposed to the outside of the holder from the opening portion.

Further, an enzyme electrode of an example of a chemical sensor using the present invention includes: electrode portion including a pair of working electrodes and counter electrode; first film formed on one of the working electrodes, which includes polyvinyl alcohol and surface-active agent; second film formed on the other working electrode, which includes polyvinyl alcohol, surface-active agent and enzyme; and overcoat film formed on the first and second film, which comprises high polymer electrolye including pH buffer.

A voltage applying method for a hydrogen type enzyme electrode having a pair of working electrodes and counter electrode according to the present invention includes: detecting a contact of a test specimen with the enzyme electrode; keeping a potential applied to the working electrodes at a first potential of substantially zero for a first preset time; applying a second potential which is higher than a hydrogen peroxide detect potential to the working electrodes for a second preset time; dropping the second potential to a third potential below zero potential; sweeping from the third potential to a fourth potential higher than the hydrogen peroxide detect potential at a fixed rate.

Since the sensor holder for a chemical sensor is thus constructed, an increased number of chemical sensors can be contained in the sensor holder, and there is eliminated a danger of contamination and infection by the test specimen attached to other portions than the sensor element. Further, a reliable moisture-proof structure of the sensor holder is secured.

In an exemplary enzyme electrode using the present invention, diffusion of a test specimen solution is accelerated by surface-active agent contained in the first and second films. A preparatory time before the measurement starts is reduced. Further, a pH buffer contained in the overcoat film reduces a variation of the concentration of hydrogen ions in the test specimen solution.

The voltage applying method of the invention provides the useful effects comparable with those when the dissolved oxygen is increased in the test specimen solution.

BRIEF DESCRIPTION OF THE DRAWINGS

Other objects, advantages and features of the present invention will be understood when carefully reading the following detailed description in connection with the accompanying drawings. In the accompanying drawings:

FIG. 18(b) is a plan view showing another pattern of a sensor element;

DETAILED DESCRIPTION OF THE PREFERRED EMBODIMENTS

Figure 1:
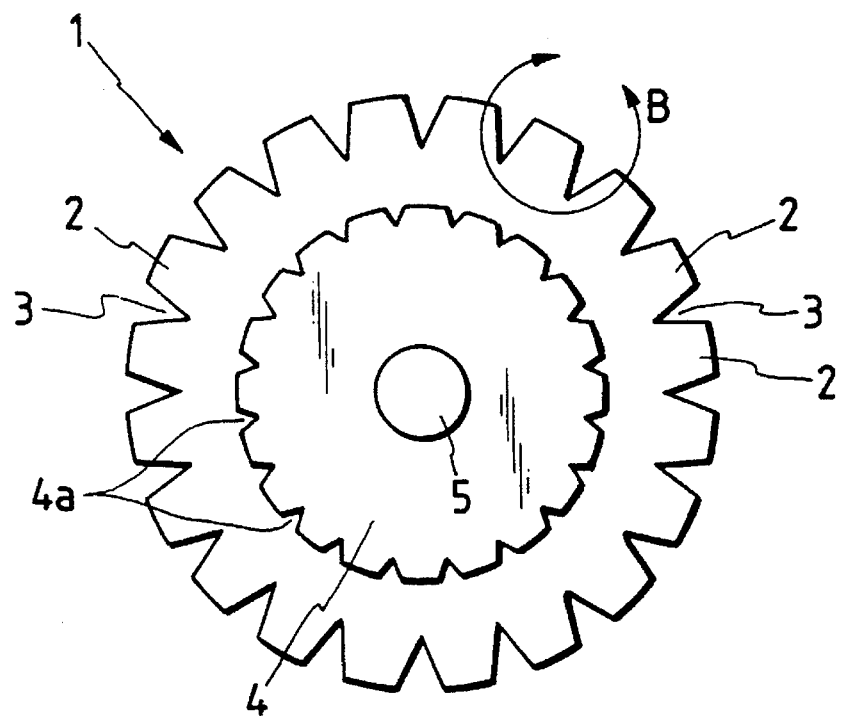
FIG. 1 is a plan view showing a first embodiment of a sensor body utilizing the present invention.

The preferred embodiments of the present invention will be described with reference to the accompanying drawings as follows. In the specification, words indicating directions, locations, and the like, such as right, left, upper and lower, are used to indicate those when viewed in the drawings. Further, throughout the drawings, like or equivalent portions are designated by like reference numerals.

Figure 2:
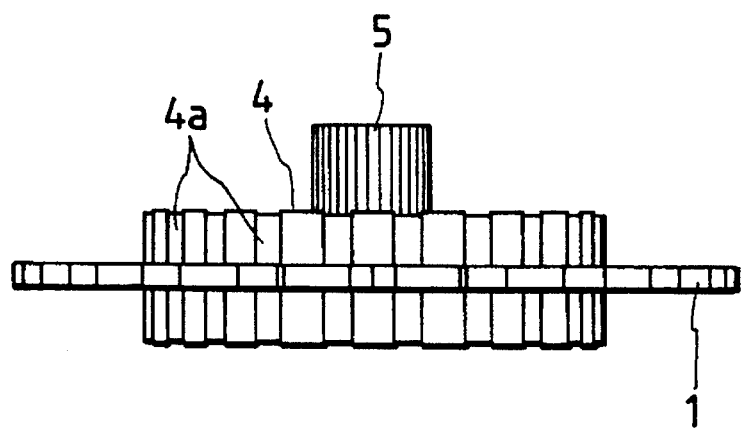
FIG. 2 is a side view showing the sensor body as shown in FIG. 1.
Figure 3:
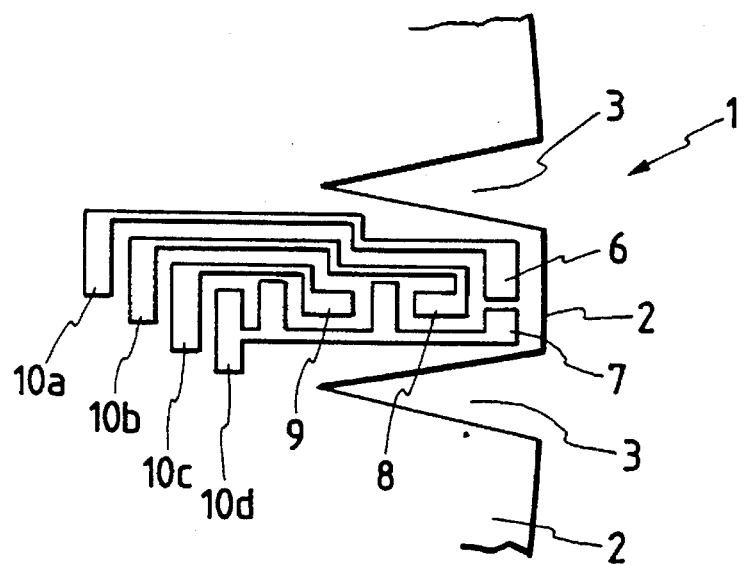
FIG. 3 is an enlarged view of the sensor body showing a sensor portion in FIG. 1 which is a construction of a sensor part of the sensor body.

A structure of a sensor is illustrated in FIGS. 1 to 3. As shown in FIG. 1, a disk-shaped sensor body 1 contains a plural number of elemental sensors 2 (referred to as sensor elements) radially extended outward from the circumference thereof. The sensor body 1 is made of a suitable insulating material, which is conventionally used for various types of substrate. The insulating material may be such plastics as epoxy resin or glass epoxy resin, or equivalent material. The circumferential portion of the sensor body 1 is shaped to have V-shaped notches 3 equidistantly and angularly arrayed therearound. Of these notches 3, the adjacent notches define a trapezoidal part. Thus, the notches 3 and trapezoidal parts are alternately arrayed on the circumference of the sensor body 1. The sensor elements 2 are formed in the trapezoidal parts, respectively.

A pattern of the sensor element 2 formed in the trapezoidal part is illustrated in detail in FIG. 3. Each of the sensor element 2 is formed by forming a circuit pattern of conductive material on the substrate, or the trapezoidal part, as of conventional sensors. A preferable conductive material may be platinum (Pt). A conventional, suitable plating technique, such as platinum plating process or conductive material printing process, may be used for forming the sensor circuit.

In the sensor circuit, a sensor portion is formed of a counter electrode 6, a reference electrode 7, a first working electrode 8, and a second working electrode 9. Reference numerals 10a, 10b, 10c, and 10d designate terminals of those electrodes. One sensor element 2 is formed by the sensor portions and the terminal portions. The sensor body 1 is shaped like a disk with the fringe made of a number of the trapezoidal parts each containing one sensor element 2 formed therein.

Reference numeral 4 designates a positioning plate coaxial with the sensor body 1. The positioning plate 4 is also used for containing desiccant therein. Accordingly, the positioning plate 4 need to be made of air-permeable material, such as plastic material with a number of perforations or air-permeable nonplastic material, e.g., hard unwoven fabric. The material have to be strong enough to withstand the operation of the positioning plate to be given later. The positioning plate 4 thus constructed is filled with desiccant. Grooves 4a are equidistantly formed in the circumferential outer face, so that the positioning plate 4 takes the form like a gear. The positioning plate 4 may consist of two half-circular plates, which are combined and fixed to the positioning-plate location on the sensor body 1. The positioning plate 4 may also be formed by fitting a positioning plate into an opening previously formed in the sensor body 1. A knob 5, which is coaxial with the sensor body 1, is provided to the surface of the sensor body 1 having the sensor element 2 formed thereon.

Figure 4:
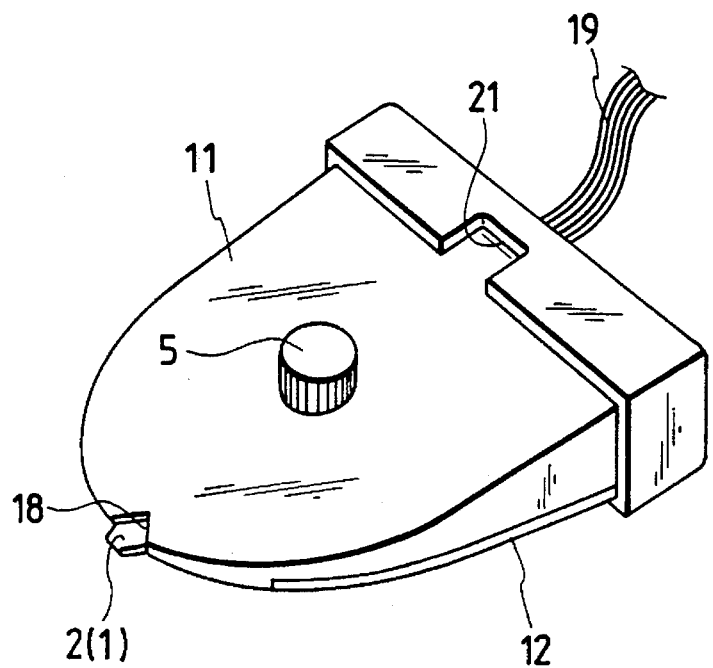
FIG. 4 is a perspective view showing au upper portion of a sensor holder housing the sensor body.
Figure 5:
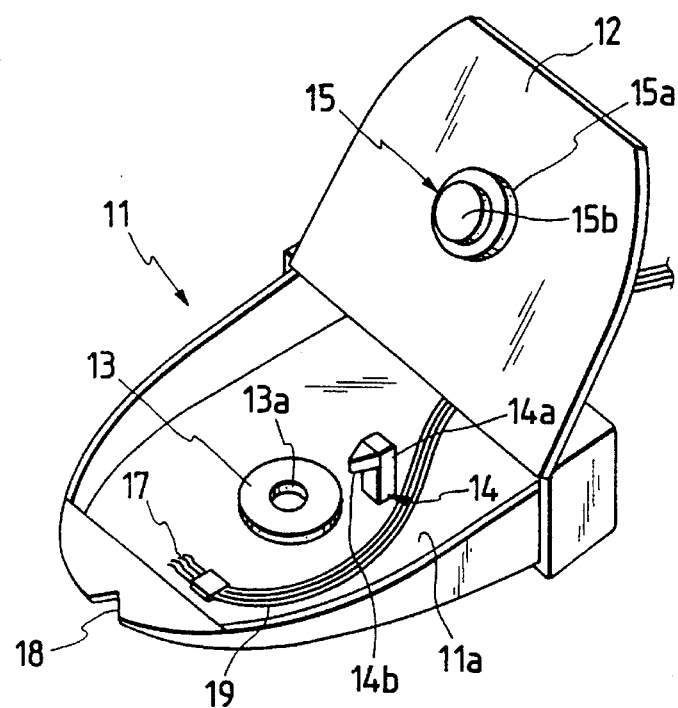
FIG. 5 is a perspective view showing the holder when a back cover thereof is opened.

FIGS. 4 and 5 shows the structure of a holder for holding the sensor body 1. FIG. 1 is a perspective view showing the upper part of the holder when it holds the sensor body 1 therein, and FIG. 2 is a perspective view showing the holder when a back cover thereof is opened, the holder being illustrated upside down.

Referring mainly to FIG. 5, a sensor holder 11 has a space where the sensor body 1 is disposed. A sensor support portion (hereinafter, referred to as a first support) 13, shaped like a ring, has an opening 13a at the central part thereof. The opening 13a is for inserting the knob. The surface of the first support 13 is formed to have a small slide resistance.

Figure 7:
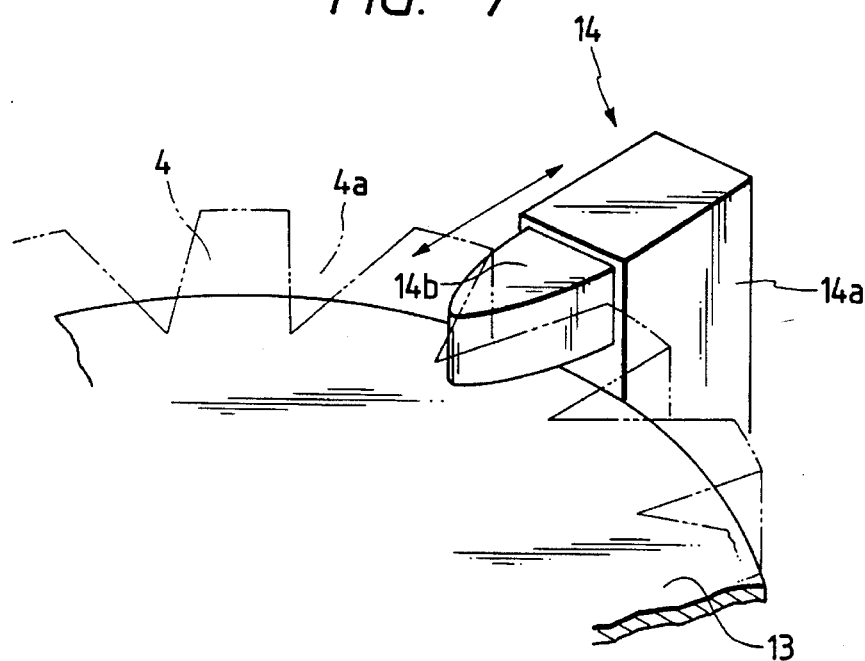
FIG. 7 is a perspective view showing how a positioning plate engages a positioning member.

A positioning member 14 is located adjacent the first support 13. The positioning member 14 includes a support 14a (referring to FIG. 7) and a stopper 14b attached to the support 14a. The support 14a is erected on the rear side of the top surface 11a of the holder 11 (in FIG. 5, the holder is illustrated with a back cover 12 thereof undermost.). The stopper 14b is constantly urged outward by a coiled spring (not shown) contained therein. The stopper 14b, when receiving a pushing force, is put into the support 14a while resisting the resilient force of the coiled spring.

Figure 6:
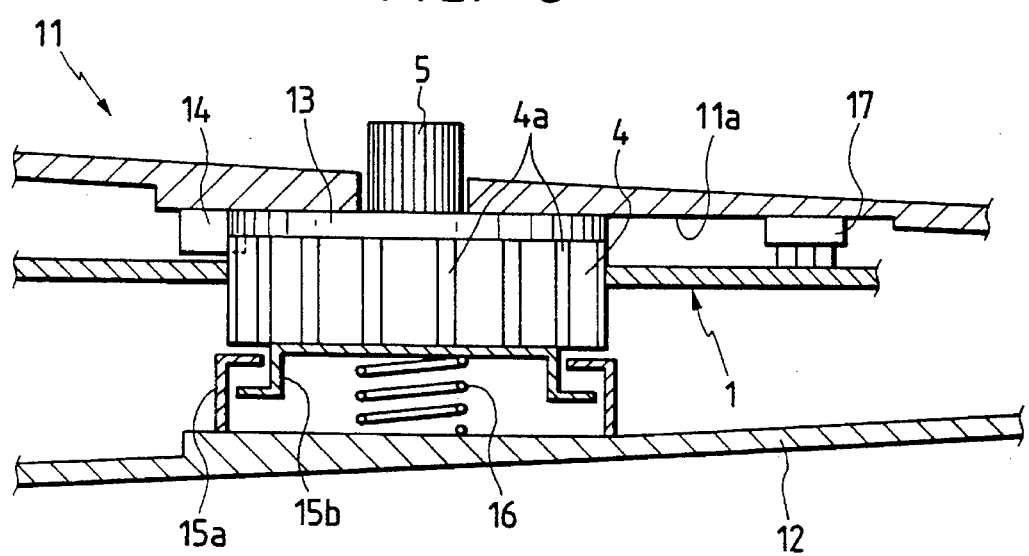
FIG. 6 is a partial cross sectional view showing the holder housing the sensor body set therein.

The back cover 12 is provided with a second support 15 as a second member for supporting the sensor body 1. The second support 15 includes a flat ring-shaped member 15a and a pushing member 15b disposed within the ring-shaped member 15a so that it is projected from the member 15a by a coiled spring 16 (FIG. 6). When the back cover 12 is closed, the second support 15 becomes coaxial with the first support 13.

As illustrated in FIGS. 4 and 5, the sensor holder 11 becomes thin toward the fore end thereof (left side in the drawing). An opening 18 of a V-shaped (as viewed from top) cutout is formed at the fore end of the sensor holder 11. The opening 18 allows only one of the sensor elements 2 of the sensor body 1 contained in the holder 11 to be exposed in the outside of the holder.

Figure 8:
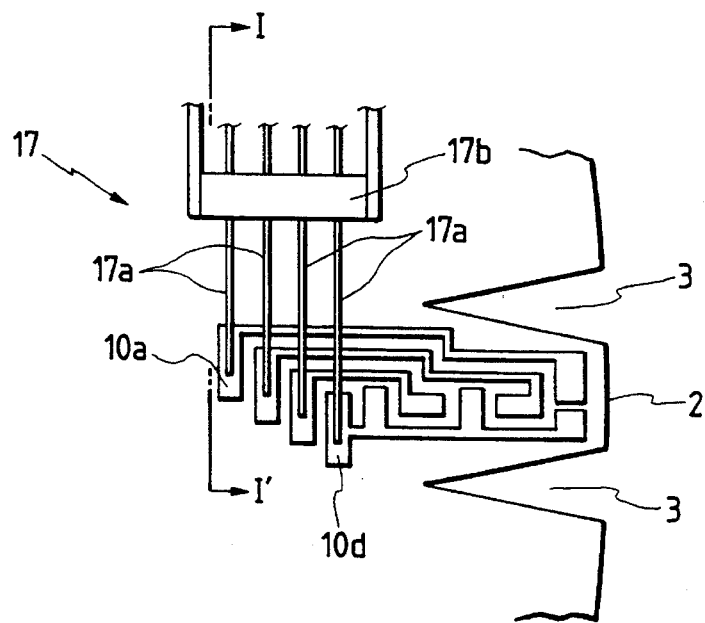
FIG. 8 is a plan view showing how a connector of the sensor holder is attached to the sensor body.
Figure 9:
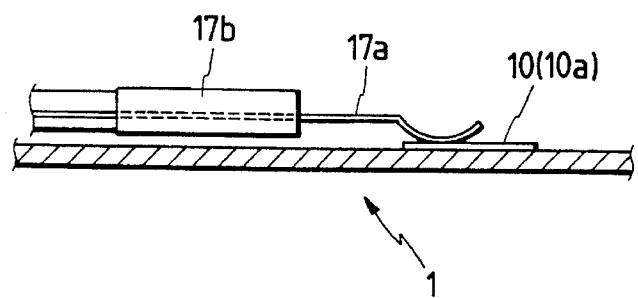
FIG. 9 is a cross sectional view taken on line I—I' in FIG. 8.

Reference numeral 17 designates a connector provided on the rear side of the top surface 11a of the holder 11. The connector 17 includes connector terminals 17a to be respectively connected to the terminals 10a to 10d of each sensor element 2, and a terminal holder 17b for holding these connector terminals (also see FIGS. 8 and 9). Cords 19 are connected at the first ends to the connector 17 while at the second ends to a measuring instrument which is not shown.

The operation and the handling of the throwaway sensor thus constructed will be described as follows.

The sensor body 1 which is not used is packed in a moisture-proof state. If the packed sensor body 1 is well sealed, the sensor body 1 can be sufficiently protected from moisture without using desiccant, which otherwise would be put into the positioning plate 4 of the sensor body 1.

At the beginning of use of the sensor body, the desiccant is removed from the sensor body 1. On the other hand, the back cover 12 of the sensor holder 11 is opened as shown in FIG. 5. The sensor body 1 is set to the holder 11 such that the sensor-element formed surface thereof is faced down (in FIG. 5), that is, the sensor elements 2 face the top surface 11a of the holder 11, and the knob 5 of the sensor body 1 is passed through the opening 13a of the first support 13 till it is protrude from the holder. In this state, the stopper 14b of the positioning member 14 engages with one of the grooves 4a of the positioning plate 4.

After the sensor body 1 is thus set in the holder, the back cover 12 is closed. In this state, as shown in FIG. 6, the pushing member 15b of the second support 15 provided on the back cover 12 is pressed against the surface of the positioning plate 4 of the sensor body 1, and cooperates with the first support to rotatably support the sensor body 1 at a given location in the sensor holder 11.

The sensor body 1 is disposed in the holder 11 such that one of the plural number of sensor elements 2 forming the sensor body 1 is partly exposed to the outside of the holder 11 (FIG. 4). More specifically, the sensor part of the sensor element, which includes the electrodes 6, 7, 8, and 9, is exposed to the outside through the V-shaped opening 18 of the sensor holder 11. The terminals 10a to 10d of the sensor element 2 the sensor part of which is exposed outside are brought into contact with the connector terminals 17a of the connector 17, respectively. As a result, this sensor element 2 is electrically connected to the measuring instrument, through the connector 17 and the cords 19. The holder 11 containing the sensor body 1 thus set therein is placed in a state that the terminals of the sensor element 2 are located on the obverse side of the holder, as shown in FIG. 4. Then, for measurement, a test piece is attached to the sensor part of the sensor element 2.

After the measurement is completed, the knob 5 is turned. With the turn of the knob, the stopper 14b of the positioning member 14 is pushed into the support 14a thereof while resisting the resilient force of the spring contained therein. When the next groove 4a reaches in front of the support 14a, the support 14a is pushed by the spring in the reverse direction and put into the groove 4a. Then, a new sensor element 2 of the sensor body 1, located adjacent the already used sensor element 2, is set at the opening 18 and comes in contact with the connector 17 as for the previous sensor. In this way, new sensor elements 2 are successively set at the opening for the successive measurements.

When the measurement progresses in this way and all of the sensor elements 2 of the sensor body 1 is used, an operator opens the back cover 12 of the sensor holder 11 so as to replace the old sensor body 1 with a new one. When the measurement is completed in a state that the sensor body 1 contains still the sensor elements 2 not yet used, the holder 11 is packed and stored in a moisture-proof state for another measurement.

In a case where the measurement is completed in a state that the sensor body 1 includes still new sensor elements 2, it is unsuggestible to take the sensor body 1 out of the holder 11. When it is taken out of the holder, the not yet used sensor elements 2 is touched with finger tips so as to reduce the reliability of the sensor elements 2. Accordingly, it is desirable to store the sensor body 1 in which the sensor body 1 has the not yet used sensor elements 2 is left to hold the sensor holder 11 therein. In the case of storing the sensor holder 11, the positioning plate 4 of the sensor body 1 preferably contains desiccant so that the inside of the holder 11 is kept in a satisfactorily dried state.

Figure 10:
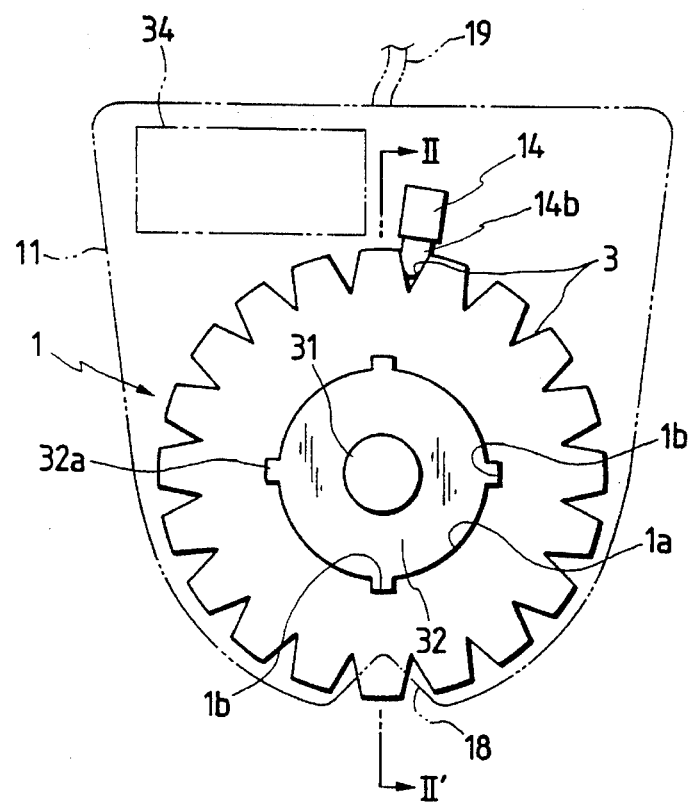
FIG. 10 is a plan view showing a sensor body according to a second example of a sensor body using the present invention.
Figure 11:
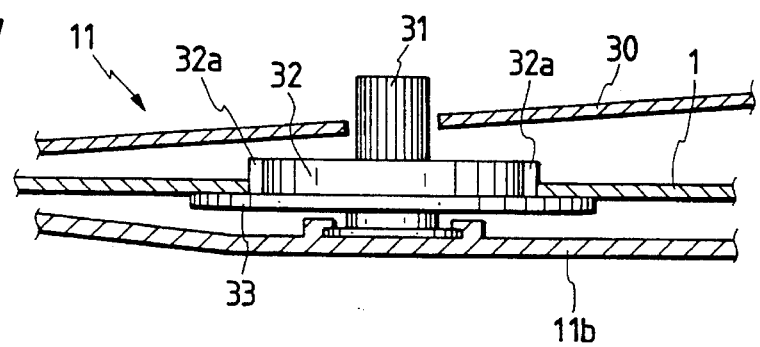
FIG. 11 is a cross sectional view taken on line II—II'.

Second embodiment of a throwaway sensor according to the present invention will be described with reference to FIGS. 10 and 11.

While the first embodiment uses the positioning plate 4 for positioning the sensor part, the second embodiment uses for the positioning device in which the fringe of the sensor body 1 is configured to have the V-shaped notches 3 and the trapezoidal parts on which the sensor elements 2 are to be formed. A sensor body 1, shaped like a ring as viewed in plan, includes an opening 1a formed at the central part and key grooves 1b formed in the side wall.

The sensor holder 11 is provided with a device for rotatably supporting the sensor body 1. A main shaft 31 is rotatably planted on a bottom plate 11b of the holder 11. The top end of the main shaft 31 serves as a knob for turning the sensor body, which corresponds to the knob 5 in the first embodiment. An engaging shaft 32 is attached to the main shaft 31. The diameter of the engaging shaft 32 is substantially equal to the inner diameter of the opening 1a of the sensor body 1. A plural number of keys 32a are protruded from the side wall of the engaging shaft 32 so as respectively to engage the key grooves 1b of the sensor body 1. A support plate 33 is coaxial with the main shaft 31 and the engaging shaft 32. The support plate 33 is larger in diameter than the engaging shaft 32. The support plate 33 supports the sensor body 1 fit to the engaging shaft 32. The positioning member 14 is mounted at a location adjacent to the circumferential edge of the sensor body 1 on the bottom plate 11b so that the stopper 14b of the positioning member 14 engages any of the notches 3. When the stopper 14b engages one of the notches 3, a sensor element 2 specified by the notch engaging the stopper is set at the opening 18 of the sensor holder 11. In other words, the positioning member 14 positions the sensor body 1 in such a way.

After the sensor body 1 is set to the holder 11, a cover 30 is closed so that the main shaft 31 is partly protruded from the cover 30. As recalled, in the first embodiment, the cover is the back cover serving as the bottom plate. In the second embodiment, the bottom plate is integral with the holder 11, and the top surface of the holder is used for the cover 30. A desiccant 34 is located within the sensor holder 11. With use of the desiccant, the sensor body 1 in the holder 11 is protected from moisture as in the first embodiment.

Figure 12:
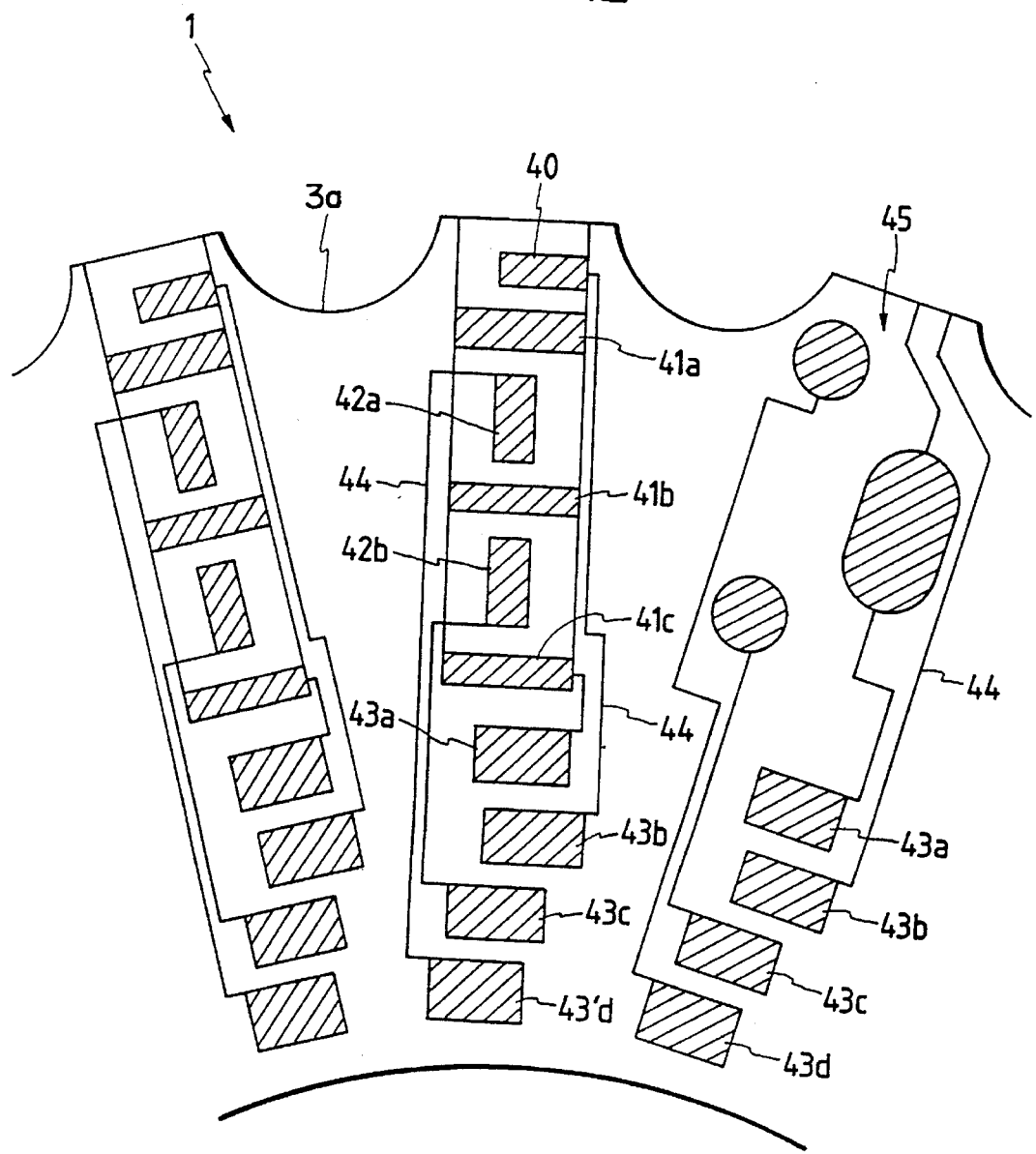
FIG. 12 is a plan view showing another sensor element.

Another construction of the sensor elements 2 (FIG. 3) will be described with reference to FIG. 12.

In the figure, a reference numeral 3a designates a notch, reference numeral 40 designates a reference electrode; 41a, 41b, and 41c, counter electrodes; 42a and 42b, working electrodes; 43a, 43b, 43c, and 43d, terminals; and 44 lead wires for connecting those electrodes. A calibrating part 45 consists of a set of electrodes (in this instance, three electrodes forms one see of the electrodes). The calibrating part 45 is formed on one of the trapezoidal parts of the sensor body 1, and is provided for calibrating the sensor.

Figure 13:
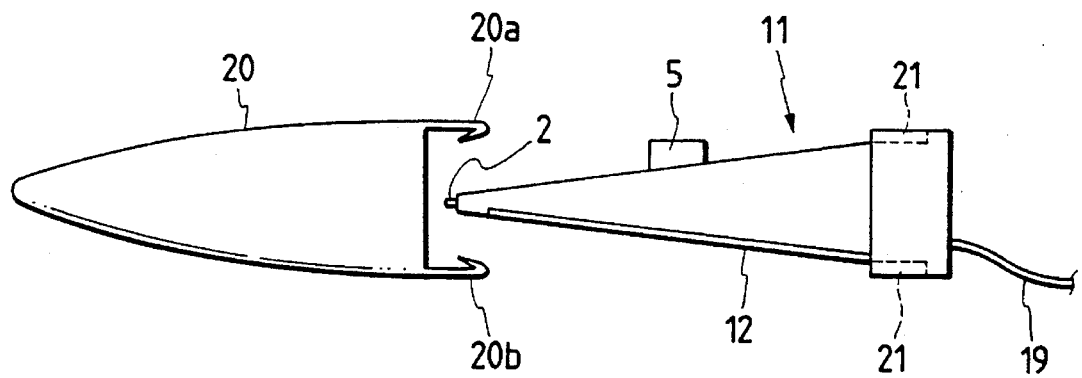
FIG. 13 shows a plan view showing a moisture-proof cap to be attached to the holder.
Figure 14:
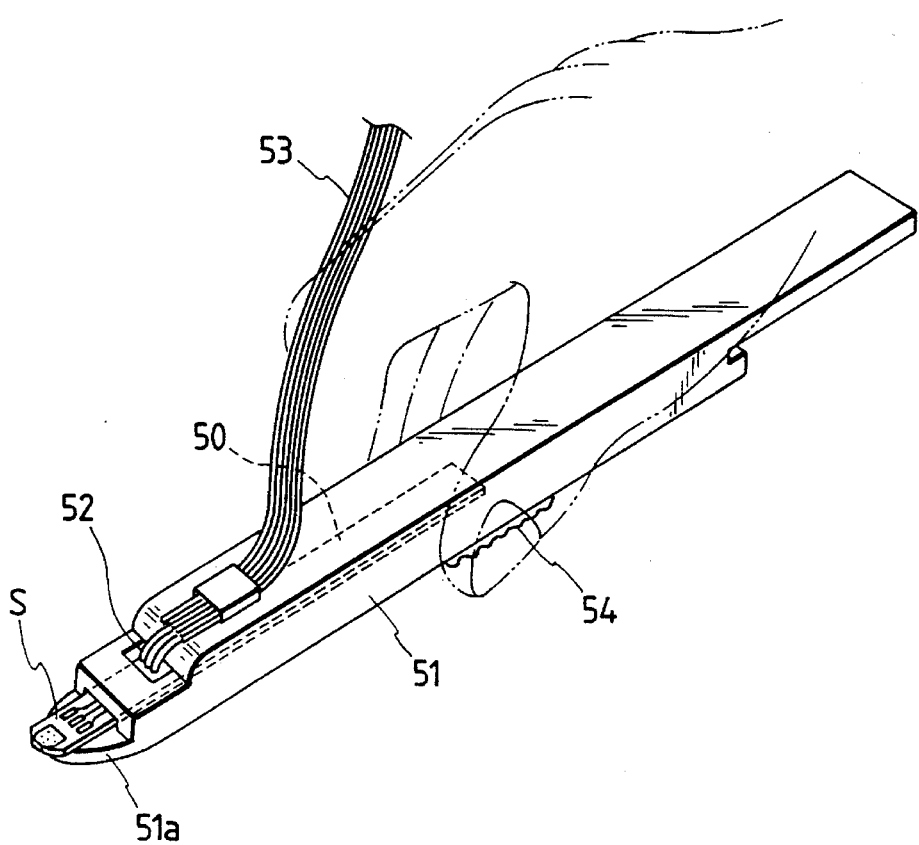
FIG. 14 is a perspective view showing a chemical sensor holder when it houses a serial type throwaway chemical sensor.

Next, FIG. 13 shows a plan view showing a moisture-proof cap to be attached to the chemical sensor holder 11. A moisture-proof cap 20 is made of high water-proof material, such as plastics. The moisture-proof cap 20 includes a pair of stopper pawls 20a and 20b formed at the opening for receiving the holder. A pair of stopper pawls 20a and 20b which is formed at the upper and lower of the holder receiving opening side, respectively, is engaged with a pair of groove 21 formed in the sensor holder 11 so that the moisture-proof cap 20 is airtightly connected with the holder 11. The moisture-proof cap 20 is very convenient for sealing the holder containing the sensor body having the not-yet-used sensor elements for a long time storage of the sensor. The moisture-proof cap 20 may also be made of water-proof and flexible material, such as rubber.

In this embodiments as mentioned above, the positioning plate 4 has two functions which are a water-proof function by desiccant and a positioning function for positioning the sensor body 1. If required, the desiccant is located at another place in the sensor holder 11, and the positioning plate 4 is used only for positioning the sensor body 1. In this case, the material of the positioning plate 4 is not limited to that referred to above.

Figure 15:
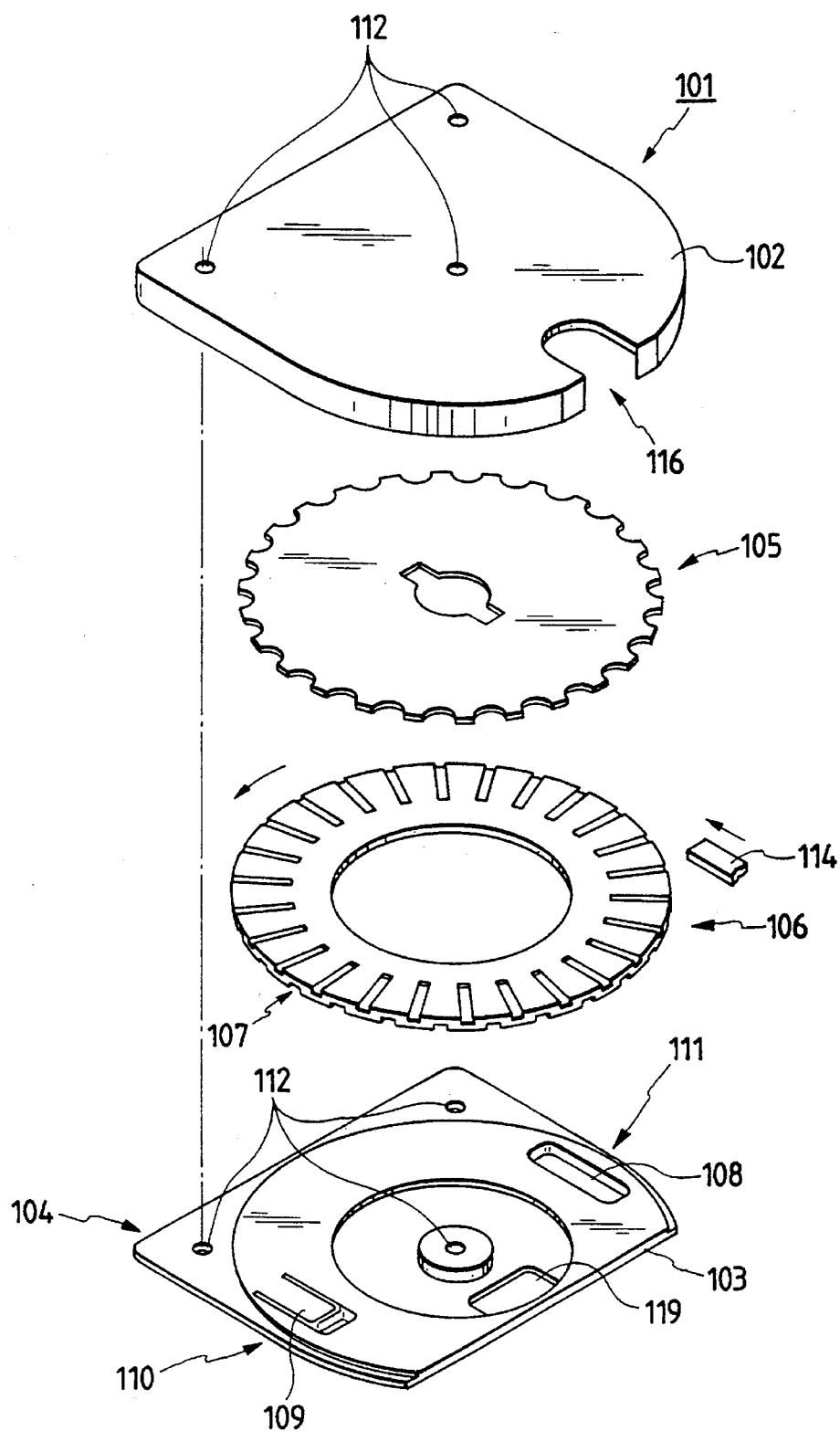
FIG. 15 is an exploded view in perspective of another exemplary chemical sensor holder using the present invention.
Figure 16:
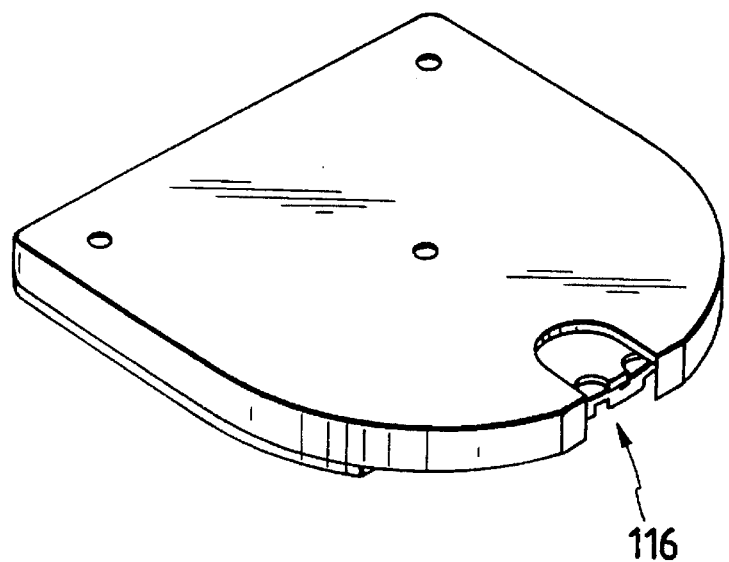
FIG. 16 is a perspective view showing the sensor holder after assembled.
Figure 17:
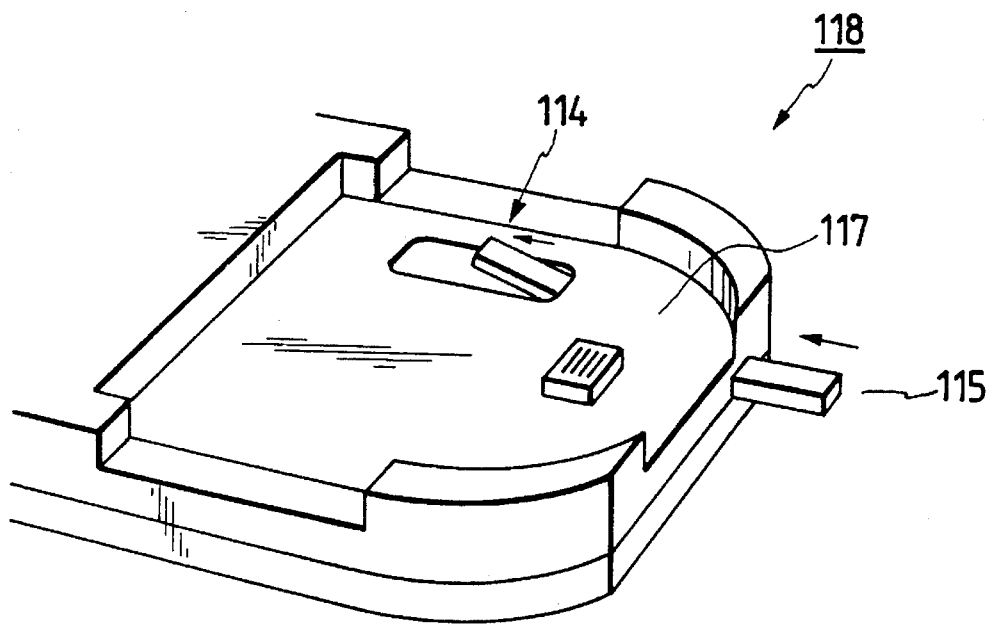
FIG. 17 is a perspective view showing a sensor feed mechanism incorporated into the sensor holder shown in FIG. 15.

FIGS. 15 to 17 show a third embodiment of a chemical sensor holder according to the present invention. FIG. 15 is an exploded view in perspective of a chemical sensor holder according to the third embodiment. In a throwaway type chemical sensor 101, a sensor jacket 104 includes an upper cover 102 with a dropping part 116 and a lower cover 103. A sensor body 105 and a sensor cover 106 bonded to the sensor body 105 are sandwiched between the upper and the lower covers 102 and 103. A number of sensor elements 144 are radially mounted on the sensor body 105 as will be described later. The sensor cover 106 includes positioning grooves 107 formed in the circumferential edge thereof. When a protrusion 114 of a holder/sensor feed mechanism 118 (FIG. 17), which will be described with reference to FIG. 17, engages one of the positioning grooves 107, the sensor body 105 is turned in a given direction. The lower cover 103 is made up of a ratchet 109 for turning the sensor body 105 every groove while preventing reversal of the turn, a pushing portion 110, a hole 108 for receiving the protrusion 114, and a sensor rotation window 111. To assembly the chemical sensor 101, the upper and lower covers 102 and 103 are coupled and fastened by countersunk screws inserted into holes 112 of the upper cover 102 and holes 112 of the lower cover 103. The chemical sensor 101 thus assembled is illustrated in FIG. 16.

The chemical sensor 101 thus assembled is set to the holder/sensor feed mechanism 118 shown in FIG. 17. The holder/sensor feed mechanism 118 is provided with a contact portion 117, a sensor lever 115 for moving the sensor, and the protrusion 114. The protrusion 114, interlocked with the sensor lever 115, is set at an initial position by a spring which is not shown. When the sensor lever 115 is pushed, the protrusion 114 is moved in the direction of an arrow, viz., in the sensor moving direction, while resisting the resilient force of the spring. When the sensor lever 115 is released, the protrusion 114 is returned to the initial position by the resilient force of the spring. The protrusion 114 is obliquely raised to have a slanted surface and a vertical surface. When the chemical sensor 101 is set to the holder/sensor feed mechanism 118, the protrusion 114 engages at the vertical surface one of the positioning grooves 107 through the hole 108, and turns the disk-shaped sensor cover 106 unidirectionally. The contact portion 117 is brought into contact with the terminals of each sensor element on the sensor body 105 through a contact window 119. One of the sensor elements arrayed on the sensor body 105 is located at the dropping part 116 (FIG. 16). A test specimen is dropped onto the exposed sensor element. The result is transferred in the form of an electrical signal to a measuring instrument which is not shown.

Figure 18A:
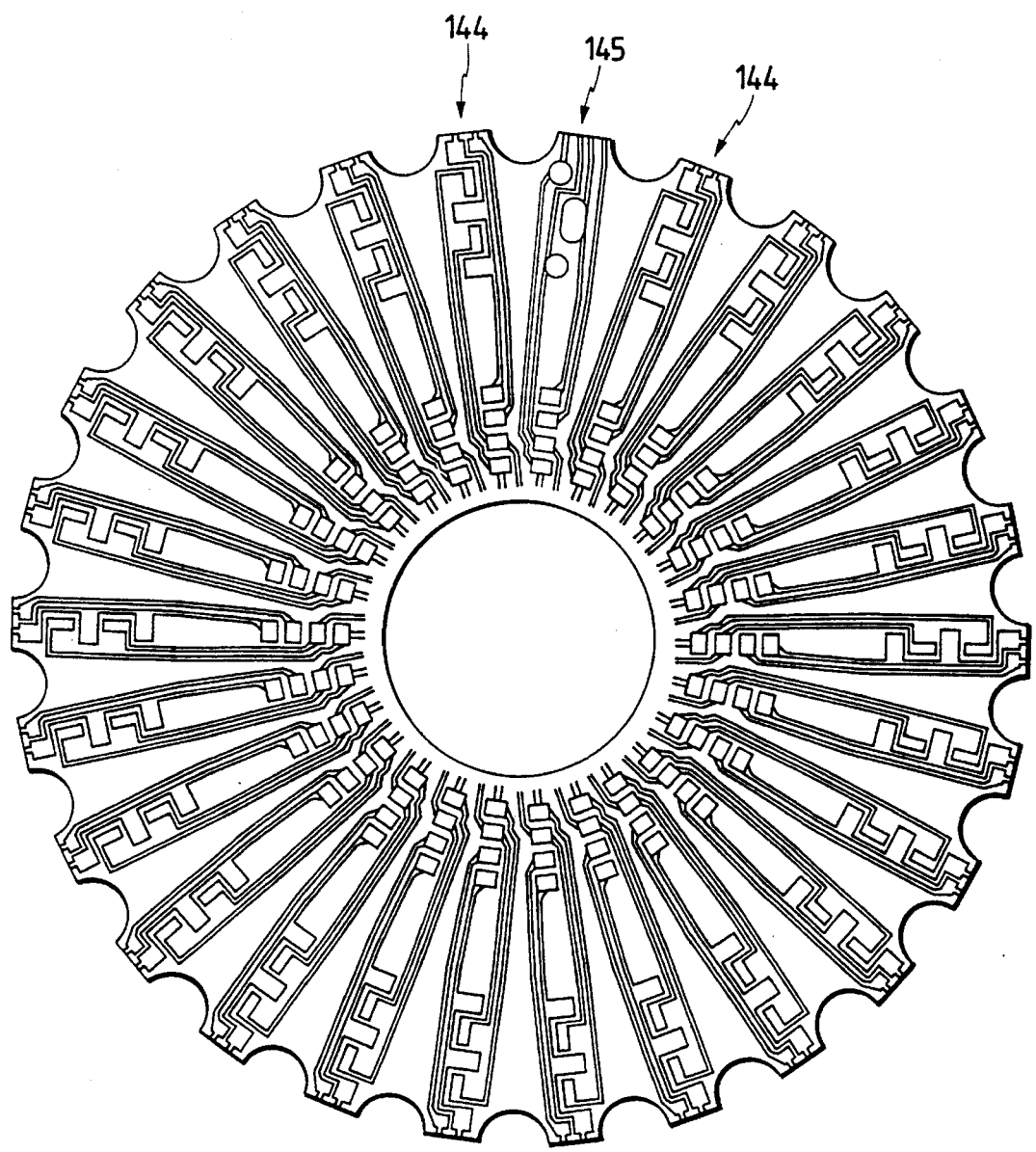
FIG. 18(a) is a plan view showing another exemplary sensor body using the present invention.

A construction of the sensor body 105 of the throwaway chemical sensor is as shown in FIGS. 18(a) and 18(b). A plural number of sensor elements 144 each as shown in FIG. 18(b) are radially formed on a disk-shaped support member. As shown in the drawings, each of the sensor elements 144 includes a reference electrode 140, its terminal 143b, counter electrodes 141a, 141b, and 141c, first and second working electrodes 142a and 142b, and their terminals 143c and 143d. The functions of these electrodes have already been described in the above-mentioned embodiments, and hence no further description thereof will be given. The sensor body 105 has also a calibrating part 145 as in the previous embodiment. The calibrating part 145 also consists of a set of electrodes (in this instance, three electrodes forms one set of the electrodes). The calibrating part 145 is formed on one of the trapezoidal parts of the sensor body 105, and is provided for calibrating the sensor.

Since the sensor elements 144 are radially disposed on the disk-like support, the number of sensor elements is increased for a fixed size of the sensor body. The sensor body have to be infrequently set to the holder for its exchange with a new one. This improves the workability and reliability of the sensor. Additionally, the troublesome work to exchange the sensor element every measurement is eliminated. Since the test specimen will not be attached to other portions than the sensor element when it is exchanged, there is eliminated danger of contamination and inflection by the test specimen mistakenly attached.

Figure 20:
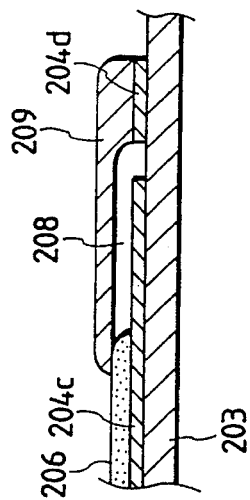
FIG. 20 is a cross sectional view taken on line III—III in FIG. 19(b)

A specific enzyme electrode as a chemical sensor, which is adaptable for the sensor holders of the present invention as mentioned above, will be described with reference to FIGS. 19 to 21. A plural number of the enzyme electrodes may be serially arrayed on a strip-shaped sensor body, as shown in FIG. 19(b) or radially arrayed on a disk-shaped sensor body as shown in FIG. 1 or 15. As a matter of course, it may be used as a single enzyme electrode as shown in FIG. 19(a).

Figure 19A:
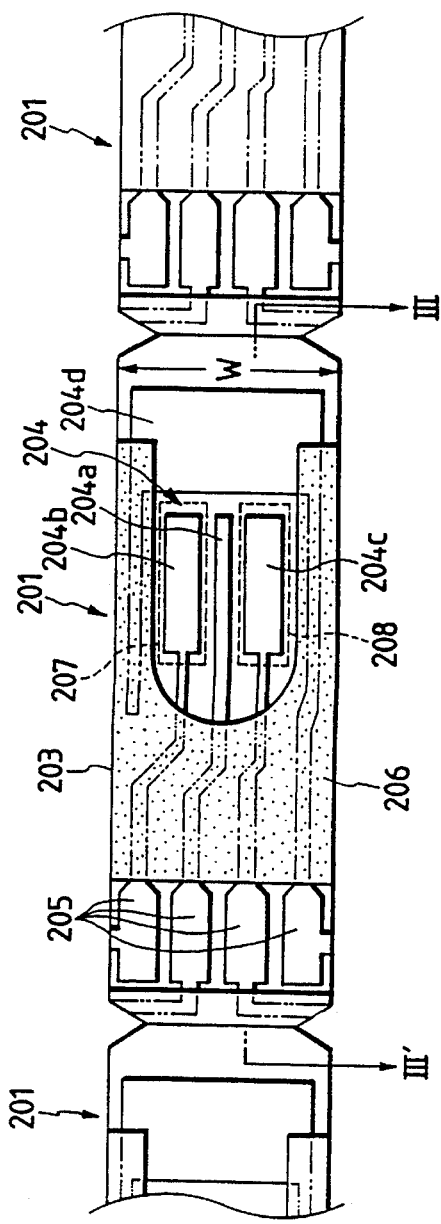
FIG. 19(a) is a plan view showing an enzyme electrode using the present invention.
Figure 19B:
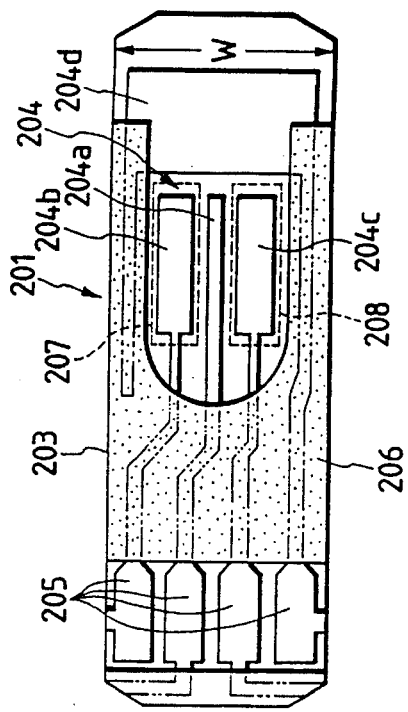
FIG. 19(b) is a plan view showing an enzyme electrode collected body containing a plural number of the enzyme electrodes of FIG. 19(a), which are serially arrayed on the enzyme electrode collected body.

Referring to FIG. 19(a), there is shown an enzyme electrode according to the present invention. In the drawing, the enzyme electrode 201 includes an electrode portion 204 of a predetermined pattern, which is formed on an insulating substrate 203 by etching process, for example. The electrode portion 204 of the enzyme electrode 201 includes a reference electrode 204a located at the central part on the insulating substrate 203, first and second working electrodes 204b and 204c located on both sides of the reference electrode 204a, and a counter electrode 204d located on the right side of the working electrodes 204b and 204c. The counter electrode 204d has upper and lower connection wires extended from the top and bottom of the left side thereof. The upper connection wire is extended above the first working electrode 204b and terminated before the terminals 205. The lower connection wire is extended below the second working electrode 204c and continuous to the related terminal 205.

These electrodes 204a to 204d are respectively connected to terminals 205 located on the left end portion. These terminals 205 are connected to a contact terminal of a measuring instrument, not shown, when a test specimen is subjected to a measurement. For the measurement, the test specimen is dropped on the electrode portion. An insulating film 206 having a substantially U-shaped when viewed from top, covers an area including a part of the counter electrode 204d and a portion for connecting the electrodes 204a to 204d to the terminals 205.

A first film 207 is layered on the first working electrode 204b. A second film 208 is layered on the second working electrode 204c. An overcoat film 209 (not shown) is further layered on both the first and second films 207 and 208. The first film 207 contains at least polyvinyl alcohol and surface-active agent. An example of the composition of the first film 207 is given below. In the composition, the components are expressed by weight for the unit area of 1 mm$^2$ of the film.

EXAMPLE 1

Composition of the first film 207

| | | |
|---|---|---|
| 1) | Polyvinyl alcohol of 300 to 3000 in polymerization degree | 0.3 µg to 3.0 µg |
| 2) | SDS (surface-active agent) | 0.5 µg to 1.5 µg |
| 3) | Sodium alginate | 0.12 µg to 0.4 µg |
| 4) | Phosphoric acid buffer | |
| | *Dipotassium hydrogen phosphate | 0 µg to 11.8 µg |
| | *Sodium hydrogen phosphate | 0 µg to 4.5 µg |

The reason why the polymerization degree of the polyvinyl alcohol is selected in the range of 300 to 3000 is as follows. Polyvinyl alcohol is hard to be dissolved into water, if its polymerization degree is high. Surface-active agent (SDS: dodecyl sodium sulfate) and phosphoric acid buffer are nonuniformly mixed so that the polyvinyl alcohol is separated out of the solution. Particularly, when the polymerization degree exceeds 3000, these components are separated out of a solution suitable for film formation even at the lower limit value (0.3 µg) of the composition example. The film components are nonuniformly distributed to cause an error in measurement. If its polymerization degree is low, the solubility of polyvinyl alcohol is increased so that it fails to grasp enzyme within a measuring time. As a result, the measurement reproducibility is deteriorated.

Ideally, it is desirable to keep a high buffering action also in the enzyme fixing film (polyvinyl alcohol film). However, polyvinyl alcohol is separated out as referred to above. To avoid the separation of polyvinyl alcohol, there is a limit in selecting the polymerization degree of polyvinyl alcohol. When the polymerization degree of the polyvinyl alcohol is 300, SDS, sodium alginate, dipotassium hydrogen phosphate, and sodium hydrogen phosphate may be contained up to the upper limit values (3.0 µg).

When the polymerization degree of polyvinyl alcohol is 3000, these components may be contained only up to the lower limit value (0.3 µg). In consideration of the polymerization degree in connection with the measuring time, for a long measuring time, the polymerization degree is desirably high, while for a short measuring time, it is desirably low. The reason why the content of the polyvinyl alcohol is selected to be between 0.3 µg and 3.0 µg will be described. The polyvinyl alcohol of high polymerization degree (3000), even if its amount is small, has a strength high enough to satisfactorily hold enzyme during the measuring time. If its amount is too small, however, it cannot grasp a necessary amount of enzyme, so that the enzyme is eluted. Accordingly, the minimum content of the polyvinyl alcohol is 0.3 µg.

When the polymerization degree of the polyvinyl alcohol is low (300), the absorption rate of the polyvinyl alcohol is higher than that when it is high. Therefore, a large amount of enzyme can be grasped by increasing the thickness of the first film. If the film is too thick, its response speed varies, leading to deterioration of the measuring accuracy. This unwanted variation of the response speed becomes remarkable when its content is in excess of 3.0 µg. To avoid this, the content of the polyvinyl alcohol is set to below 3.0 µg.

The second film 208 contains at least polyvinyl alcohol, surface-active agent, and enzyme. An example of the composition of the film contains glucose oxidase of 0.5 units/mm$^2$ in addition to the composition of the first film 207.

The overcoat film 209 contains at least high polymer electrolyte containing pH buffer. An example of the composition of the overcoat film is shown below.

EXAMPLE 2

Composition of the overcoat film 209

| | | |
|---|---|---|
| 1) | Sodium alginate (high polymer electrolyte) | 5 µg to 20 µg |
| 2) | Phosphoric acid buffer composition by molar ratio | |
| | *Dipotassium hydrogen phosphate: Sodium hydrogen phosphate (sodium phosphate) = 1:1 to 9:1 | |
| | *Dipotassium hydrogen phosphate | 32 µg to 236 µg |
| | *Sodium hydrogen phosphate | 4.5 µg to 90 µg |

The high polymer electrolyte of the overcoat film 209 may be any other suitable material than alginic acid, for example, polystyrene sulfonic acid or polyacrylic acid. The surface-active agent used for the first and second films 207 and 208 may be any other suitable material than SDS, e.g., any of negative ion active agents, such as higher fatty acid alkaline salts and alkyl aryl sulfonic acid salts, or any of nonionic surface-active agents, such as polyethylene glycol alkyl phenyl ether and sorbitan fatty acid ester.

The pH buffer may be not only the phosphoric acid but also a reagent satisfying the following conditions. Positive ions having a valence of 2 or more are not contained. When it is dissolved into a test specimen solution, the concentration of hydrogen ions is between 5 and 8. The reagent does not hinder the enzyme reaction and the electrode reaction. Use of the pH buffer not containing the positive ions having a valence of 2 or more is preferable since the pH buffer containing such positive ions makes the coating work of gelatinized alginic acid difficult.

A further description of the overcoat film 209 will be given. The quantity of the sodium alginate is determined by the thickness of the film and a mixing ratio of the sodium alginate and the buffer at which a uniform distribution of the buffer is secured. If the buffer is nonuniformly distributed in the sodium alginate, much time is taken for dissolving the buffer into the sodium alginate so that the concentration distribution varies. The variation of the concentration distribution adversely affects the measuring accuracy. A high buffering action is desirable; however, it must be properly selected allowing for the measuring accuracy and the measuring time. The quantity of the sodium alginate determines the thickness of the overcoat film. If the film is too thick, time taken for the film to absorb the test specimen solution is long. Conversely, if it is too thin, the separation ability of protein substance and blood corpuscles from the test specimen solution becomes lower so that the measuring accuracy is also worsened. Generally, this type of the electrode is designed such that the absorbing time of the test specimen solution is within one minute.

In the example of the composition of the overcoat film 209, dipotassium hydrogen phosphate and sodium hydrogen phosphate are used, because the pH value, as desired, can be changed by adjusting the composition ratio of these materials. When these materials are mixed, at 1:1, in the sodium alginate, the pH value which indicates a buffering action can be adjusted to be 5.2. When these materials are mixed at 9:1, the adjusted pH value is approximately 7.8. Thus, by properly selecting the quantity of the buffer and the composition ratio of the buffering materials, an activity of the enzyme is controlled, whereby a calibration curve can be changed.

When the composition ratio is 1:1 and the quantity of the buffer is low, the sensitivity of the sensor is increased at a low substrate concentration, but it is decreased at a high substrate concentration. When the composition ratio is 9:1 and the quantity of the buffer is high, the sensitivity is decreased at a low substrate concentration, but it is increased at a high substrate concentration.

A specific example of an enzyme electrode according to the present invention will be described.

An enzyme electrode structured like the enzyme electrode 201 shown in FIG. 1 was manufactured. First and second films 207 and 208, and an overcoat film 209 were fabricated at the following composition ratios. Those films fabricated were layered on an electrode portion 204. In the following composition ratios, the respective components are expressed at the ratios in distilled water of 1 ml.

A. Components of the first film 207

| 1) | Polyvinyl alcohol of 500 in polymerization degree | 2.8 mg/ml |
|---|---|---|
| 2) | SDS (surface-active agent) | 2.5 mg/ml |
| 3) | Sodium alginate | 0.5 mg/ml |
| 4) | Phosphoric acid buffer | 30 mM |
|  | *Dipotassium hydrogen phosphate | 3.5 mg/ml |
|  | *Sodium hydrogen phosphate | 1.2 mg/ml |

B. Components of the second film 208

The second film 208 includes glucose oxidase of 500 units/ml in addition to the components of the first film 207.

C. Components of the overcoat film 209

| 1) | Sodium alginate (high polymer electrolyte) | 10 mg/ml |
|---|---|---|
| 2) | Phosphoric acid buffer<br>Phosphoric acid buffer composition by molar ratio<br>*Dipotassium hydrogen phosphate:<br>Sodium hydrogen phosphate (sodium phosphate) = 2:1 | 0.6 M |

| *Dipotassium hydrogen phosphate | 116 mg/ml |
|---|---|
| *Sodium hydrogen phosphate | 40 mg/ml |

The first working electrode 204b was coated with the thus prepared film material of the first film 207 of 2 μl, by a dispenser. Thereafter, it was placed in a desiccator to be dried for 20 minutes. The second working electrode 204c was coated with the same amount of the thus prepared film material of the second film 208 to be dried in the same conditions. Thereafter, the first and second films 207 and 208 were coated with the thus prepared film material of the overcoat film 209 of 8 μl, and dried for one hour or longer.

Figure 21:
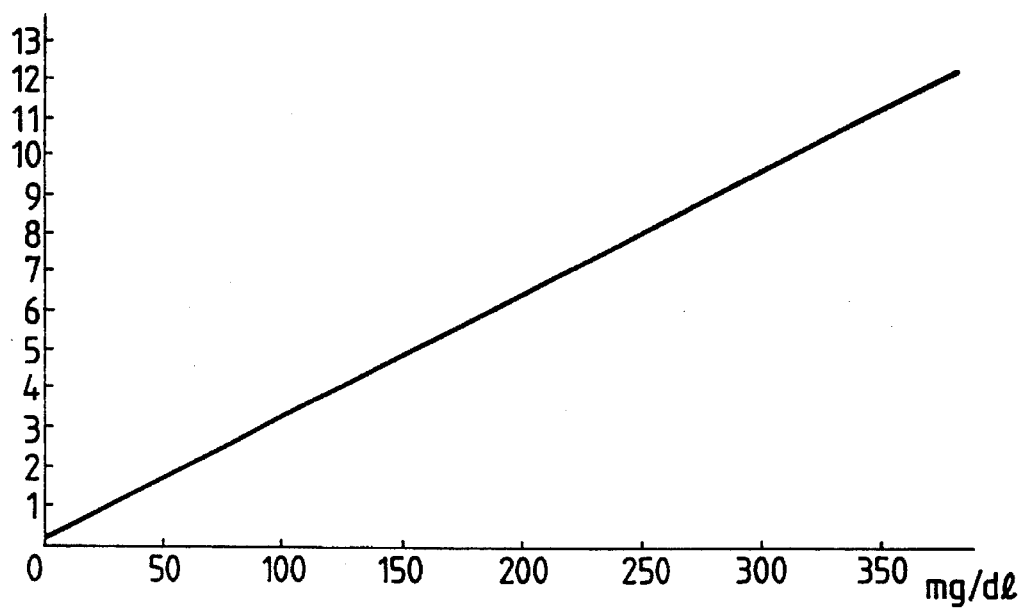
FIG. 21 is a graph showing a calibration curve of the enzyme electrode using the invention.

An occult blood as a test specimen solution was dropped on the enzyme electrode thus manufactured. The resultant calibration curve was as shown in FIG. 21. As seen from the drawing, the calibration curve of the enzyme electrode of the invention has an excellent linearity.

From the foregoing description, in the enzyme electrode of the invention, the first film formed on the first working electrode contains surface-active agent. With the use of the surface-active agent, diffusion of the test specimen solution is accelerated by the surface-active agent. A preparatory time before a measurement starts is reduced. Further, since the overcoat film contains pH buffer, if the substrate in the test specimen solution reacts with the dissolved oxygen to generate hydrogen, a variation of the concentration of hydrogen ions is reduced by the pH buffer, thereby providing a high accuracy of measurement.

Further, in the enzyme electrode of the hydrogen peroxide type, which includes the enzyme electrode of the invention, a range allowing a substrate to be measured is limited by the dissolved oxygen in the test specimen solution. To expand this range, the inventor excogitated some inventive and unique methods of applying voltage to the enzyme electrode, which can expand this range. These methods applied to the electrode will be described with reference to FIGS. 22 to 25.

Figure 22:
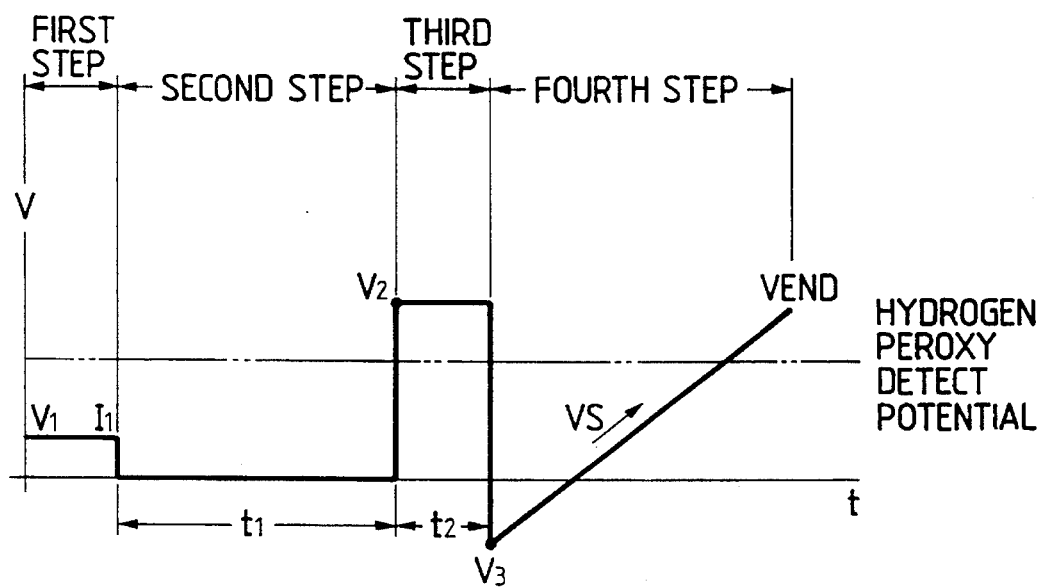
FIG. 22 is a graph explaining a first method of applying voltage to the enzyme electrode according to the present invention.

FIG. 22 is a graph showing a first method of applying voltage to the enzyme electrode. The voltage applying method includes first to fourth steps. The first step is for detecting the contact of a test specimen with the enzyme electrode 201. To detect this contact, a positive potential $V_1$ is applied to the first and second working electrodes 204b and 204c. Current $I_1$ flowing a path between the first and second working electrodes 204b and 204c and the counter electrode 204d is detected.

The potential $V_1$ applied to the first and second working electrodes 204b and 204c may be negative in polarity. The amplitude of the potential $V_1$ is preferably as low as possible in order to minimize an adverse influence on the electrodes and the enzyme films. The polarity of the current $I_1$ depends on a state of the electrode and the direction of impregnating the test specimen into the electrodes. Therefore, it is desirable to use a current detecting device capable of detecting positive and negative currents.

A second step, following the first step, keeps the potential applied to the sensor at a first potential for a preset time $t_1$ at which no current flows into the first and second working electrodes 204b and 204c. In using the enzyme electrode 201 as the throwaway chemical sensor, after the test specimen is dropped on the electrode portion 204, it is necessary to sufficiently adapt the dropped test specimen to the enzyme films and others such as reagent in an enzyme reaction area on the surface of the electrode portion 204. Accordingly, a time zone is provided where no current flows into the electrode portion 204 for the preset time $t_1$ after the test specimen is detected.

The first potential for causing no current to flow into the electrode portion 204 may be realized by setting the potential applied to the electrode portion 204 at substantially 0, or disconnecting a potential applying device (power source) from the electrode portion 204. At this time, the same may also be realized by using such a voltage as to cause an extremely smaller current than the measurement detection current. The preset time $t_1$, usually 15 to 40 seconds, preferably 30 to 40 second, is determined by the composition and the thickness of the enzyme film, the structure of the electrode, and the like. This time may be reduced by reducing the film thickness as thin as possible, constructing the electrode structure as to swiftly guide the test specimen onto the surface of the enzyme film, using such a material as to well absorb the test specimen, or the like.

A third step, following the second step, is to apply a second potential $V_2$, which is higher than a hydrogen peroxide detect potential (indicated by a phantom line in FIG. 22), to the first and second working electrodes 204b and 204c for another preset time $t_2$, and to drop the potential to a third potential $V_3$ below zero potential. In this instance, the hydrogen peroxide detect potential is approximately 600 mV, although it depends on the structure of the electrode portion 204.

The time $t_2$ for applying the second potential $V_2$ is preferably as short as possible in order to remove adverse effects on the reproducibility of the measuring current, although it depends on the amplitude of the second potential $V_2$. The third potential $V_3$ may be any potential if it is below zero potential; however, if the hydrogen peroxide detect potential is 600 mV, the third potential is preferably set to a potential 800 to 100 mV lower than the hydrogen peroxide detect potential.

In a fourth step following the third step, the potential applied to the first and second working electrodes 204b and 204c is swept up from the third potential $V_3$ to a fourth potential $V_{end}$ higher than the hydrogen peroxide detect potential, at a fixed rate Vs. The sweeping rate Vs may be set at a proper value, preferably substantially 100 mV/sec. A peak value of current in the range of the voltage sweep up to the fourth potential Vend, a current value at a potential separated from the potential causing the peak current value by a preset potential value, or a current value at a specific potential is detected, and the detected current value is converted into a concentration of a substance under measurement by using a calibration curve previously charted.

The voltage applying method produces the results comparable with those when the dissolved oxygen is increased, as will be seen from the experiment results. Although the mechanism causing such results cannot be clearly explained at present stage, it is thought that the electrolysis progresses under the applied voltage to supply enzyme and hence to expand a range allowing the concentration of the substance under measurement to be measured.

Figure 23:
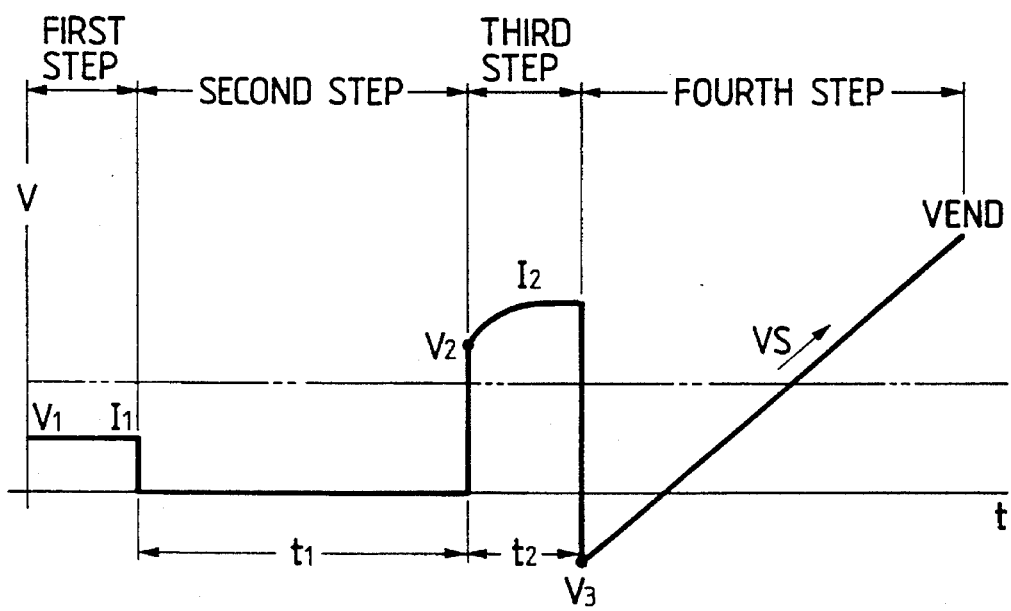
FIG. 23 is a graph explaining a second method of applying voltage to the enzyme electrode according to the present invention.

FIG. 23 is a graph explaining a second method of applying voltage to the enzyme electrode according to the present invention. Only the different portions of the second voltage applying method from the first voltage applying method will be described. The second voltage applying method includes first to fourth steps as the first voltage applying method. Of those steps, the first, second, and fourth steps are the same as those of the first voltage applying method.

In the third step, a potential causing a large fixed current $I_2$ is applied to the first and second working electrodes 204b and 204c for a preset time $t_2$, and then the potential is decreased to the third potential $V_3$ below zero potential. The fixed current $I_2$ is larger than an expected peak hydrogen peroxide detect current. Where the measurable maximum concentration of glucose is 500 mg/dl, the current corresponding to the concentration is the expected peak hydrogen peroxide detect current (in this instance, it is set at approximately 40 µA). In this step, the current control is carried out. Accordingly, the second voltage applying method is suitable for the chemical sensor in which the reference electrode 204a and the first and second working electrodes 204b and 204c are made of the same material. The reference potential at the reference electrode 204a depends on the components of the test specimen, and indicates a relative potential.

In this case, if the equal potential is applied to the sensor plural times, the same electrode reaction does not always recur. In a measurement, the hydrogen peroxide detect voltage is 600 mV and in another measurement it may be 800 mV. The voltage applying method in which a fixed voltage is applied to the sensor is unsatisfactory in providing a good measurement reproducibility. To cope with this, the second voltage applying method uses the step to flow a fixed current $I_2$ into the sensor for a fixed time $t_2$. With this step, a quantity of chemical reaction at the electrodes is controlled to be constant so that the measurement reproducibility is improved. The fixed time $t_2$ is set under the conditions similar to those in the first voltage applying method.

Figure 24:
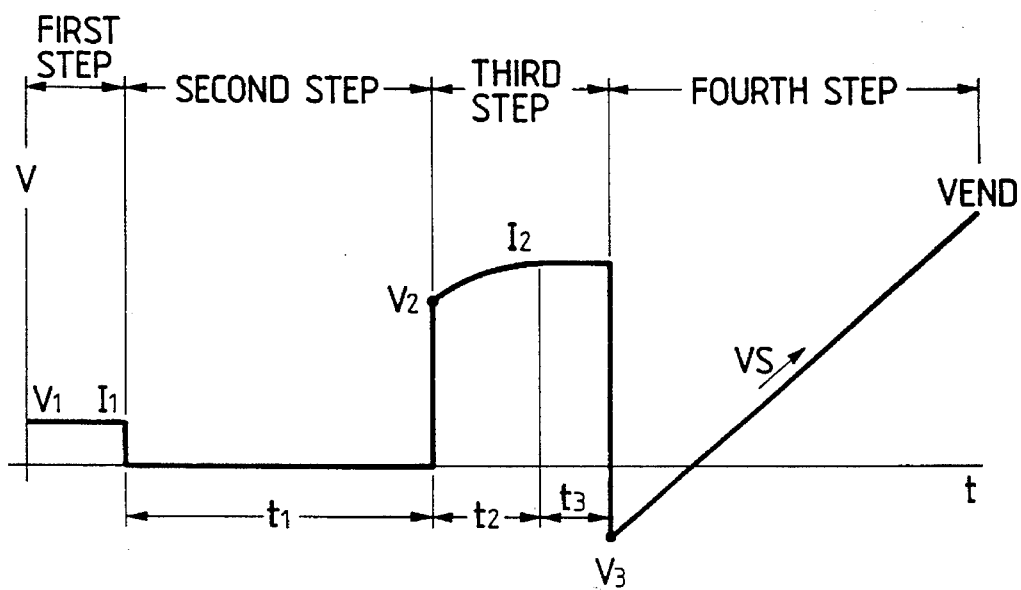
FIG. 24 is a graph useful in explaining a third method of applying voltage to the enzyme electrode according to the present invention.

FIG. 24 is a graph explaining a third method of applying voltage to the enzyme electrode according to the present invention. Only the different portions of the third voltage applying method from the first and second voltage applying methods will be described. The third voltage applying method includes first to fourth steps as the first and second voltage applying methods. Of those steps, the first, second, and fourth steps are the same as those of the first and second voltage applying methods.

In the third step, a potential causing a current larger than a hydrogen peroxide detect current is applied to the first and second working electrodes 204b and 204c for a preset time $t_2$. Succeedingly, the potential that is reached when the time duration terminates is kept for a preset time $t_3$. Finally, the potential is decreased to the third potential $V_3$ below zero potential. The measuring time of the third voltage applying method is slightly longer than that of the first and second ones. However, the third voltage applying method can expand a range allowing the concentration of the substance under measurement to be measured, and improve the measurement reproducibility.

Figure 25:
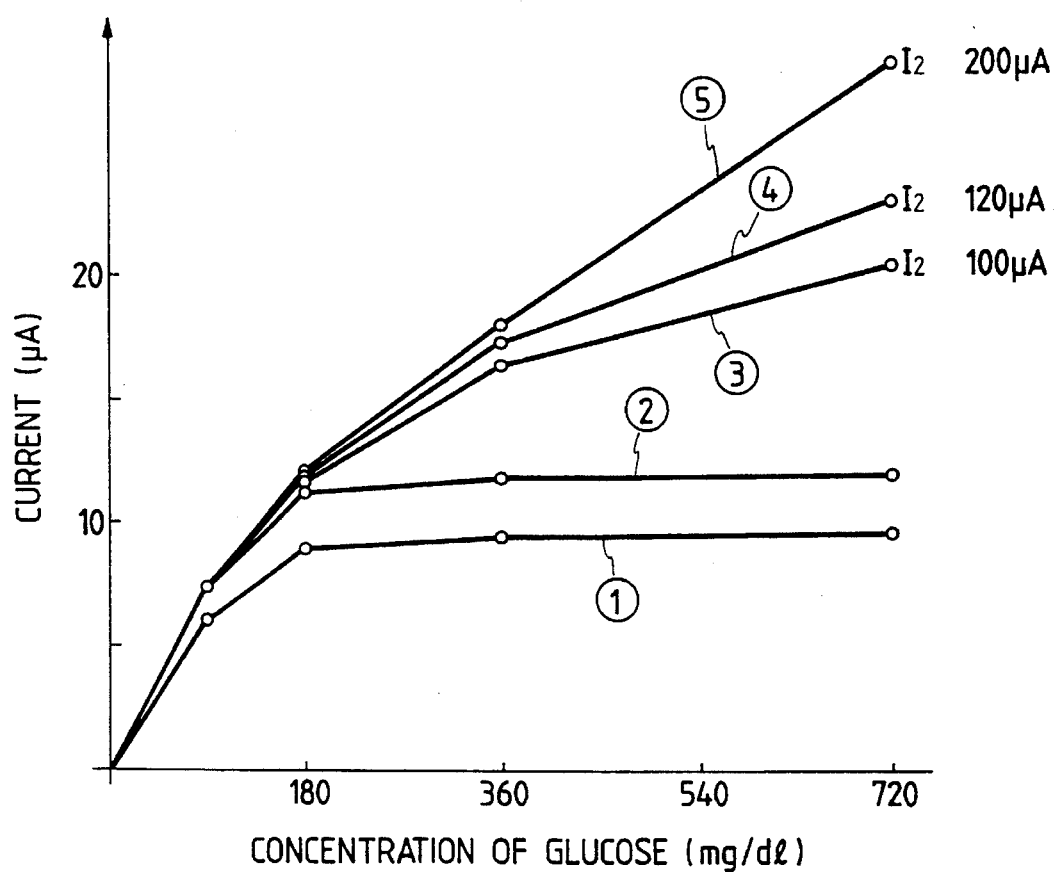
FIG. 25 is a graph showing the results of an experiment for confirming the useful effects attained by the third voltage applying method.

FIG. 25 is a graph showing the results of an experiment for confirming the effects of the voltage applying methods described above. In the experiment, enzyme electrodes of the composition ratios as mentioned above were manufactured and tested under the following conditions.

The width w and the length l of each of the first and second working electrodes 204b and 204c were: w=0.5 mm and l=2.5 mm. A test specimen was the blood of a cattle. EDTA2kl of 3 mg/ml was added to the blood to adjust the glucose. Voltage, Current or time which was applied in the experiment is indicated as follows.

$V_1$: 200 mV $I_1$: 5 µA $t_1$: 20 sec $V_2$: 1500 mV $I_2$: 100, 120, 200 µA $t_2$: 5 sec $t_3$: 2 sec $V_3$: −400 mV Vs: 100 mV/sec The curves of FIG. 25 were plotted when voltage was applied to the sensor by the third voltage applying method.

In the graph, a curve (1) was plotted in a condition that the third step of the third voltage applying method was omitted, and in the fourth step voltage was increased from 0. A curve (2) was plotted when the potential $V_3$ was set at 0. Curves (3) to (5) were plotted when the current $I_2$ in the third step was set at 100, 120, and 200 µA.

As seen from FIG. 25, in the curve (1), the glucose concentration is saturated at 180 mg/dl. On the other hand, when the voltage $V_3$ is set to below 0 V and the current $I_2$ is increased, the saturation value of the glucose concentration is increased, thereby expanding the measurable range.

According to the foregoing description, the voltage applying methods of the present invention can expand the measurable range without making the structure of the enzyme electrode complicated.

What is claimed is:

1. A voltage applying method for a hydrogen enzyme electrode having a pair of working electrodes, a reference electrode and a counter electrode comprising:

detecting a contact of a test specimen with said enzyme electrode;

keeping a potential applied to said working electrodes at a first potential of substantially zero for a first preset time;

applying a second potential which is higher than a hydrogen peroxide detect potential to said working electrodes for a second preset time;

dropping said second potential to a third potential below zero potential;

sweeping from said third potential to a fourth potential higher than said hydrogen peroxide detect potential at a fixed rate.

2. A voltage applying method according to claim 1, wherein said detecting step comprising:

applying a preset potential to said pair of working electrodes;

detecting a preset current between said pair of working electrodes and said counter electrode to confirm as to whether enzyme electrode contacts said test specimen.

3. A voltage applying method according to claim 1, wherein said first preset time is substantially 15 to 40 seconds.

4. A voltage applying method according to claim 1, wherein said hydrogen peroxide detect potential is substantially 600 mV.

5. A voltage applying method according to claim 4, wherein said third potential is substantially −400 to −200 mV.

6. A voltage applying method according to claim 1, wherein said fixed rate is substantially 100 mV/sec.

7. A voltage applying method according to claim 1, further comprising said value:

simultaneously with said sweeping step, detecting one of a peak value of current in the range of the voltage sweep to said fourth potential, a current value at a potential separated from a potential causing the peak current value by a preset potential value, and a current value at a specific potential; and converting said detected current value into a concentration of a substance in said test specimen by comparing with a calibration curve previously charted.

8. A voltage applying method for a hydrogen enzyme electrode having a pair of working electrodes, a reference electrode and a counter electrode comprising:

detecting a contact of a test specimen with said enzyme electrode;

keeping a potential applied to said working electrodes at a first potential of substantially zero for a first preset time;

flowing a first current which is larger than a hydrogen peroxide detect current to said working electrodes for a second preset time;

dropping to a second potential below zero potential;

sweeping from said second potential to a third potential higher than said hydrogen peroxide detect potential at a fixed rate.

9. A voltage applying method according to claim 8, wherein said detecting step comprising:

applying a preset potential to said pair of working electrodes;

detecting a preset current between said pair of working electrodes and said counter electrode to confirm enzyme electrode contact with said test specimen.

10. A voltage applying method according to claim 8, further comprising:

simultaneously with said sweeping step, detecting one of a peak value of current in the range of the voltage sweep to said fourth potential, a current value at a potential separated from a potential causing the peak current value by a preset potential value, and a current value at a specific potential; and converting said detected current value into a concentration of a substance in said test specimen by comparing said value with a calibration curve previously charted.

11. A voltage applying method according to claim 8, further comprising, before dropping to a second potential step, keeping a final potential that is reached when said preset time is passed at a third preset time.

12. A voltage applying method according to claim 11, further comprising:

simultaneously with said sweeping step, detecting one of a peak value of current in the range of the voltage sweep to said fourth potential, a current value at a potential separated from a potential causing the peak current value by a preset potential value, and a current value at a specific potential; and converting said detected current value into a concentration of a substance in said test specimen by comparing said value with a calibration curve previously charted.

* * * * *